United States Patent
Takahashi et al.

(10) Patent No.: US 10,772,585 B2
(45) Date of Patent: Sep. 15, 2020

(54) X-RAY DIAGNOSIS APPARATUS

(71) Applicant: Toshiba Medical Systems Corporation, Otawara-shi (JP)

(72) Inventors: Kansei Takahashi, Nasushiobara (JP); Akira Mochiduki, Nasushiobara (JP); Katsuo Takahashi, Yaita (JP); Norimitsu Kosugi, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 683 days.

(21) Appl. No.: 15/178,705

(22) Filed: Jun. 10, 2016

(65) Prior Publication Data

US 2016/0361033 A1 Dec. 15, 2016

(30) Foreign Application Priority Data

Jun. 12, 2015 (JP) .................................. 2015-119678

(51) Int. Cl.
G03B 42/04 (2006.01)
A61B 6/08 (2006.01)
A61B 6/00 (2006.01)

(52) U.S. Cl.
CPC .............. *A61B 6/08* (2013.01); *A61B 6/4283* (2013.01); *A61B 6/465* (2013.01); *A61B 6/467* (2013.01); *A61B 6/545* (2013.01); *A61B 6/566* (2013.01)

(58) Field of Classification Search
CPC .......... A61B 6/542; A61B 6/463; A61B 6/461
See application file for complete search history.

(56) References Cited

U.S. PATENT DOCUMENTS

| 5,870,450 A * | 2/1999 | Khutoryansky | A61B 6/4283 378/181 |
| 10,022,093 B2 * | 7/2018 | Nagai | A61B 6/08 |
| 2003/0198317 A1 * | 10/2003 | Nakagawa | A61B 6/4405 378/62 |
| 2011/0274251 A1 * | 11/2011 | Omernick | G01T 7/00 378/98.8 |
| 2015/0230763 A1 | 8/2015 | Nagai | |

FOREIGN PATENT DOCUMENTS

| EP | 0 923 275 | 6/1999 |
| EP | 0 923 275 A2 | 6/1999 |
| EP | 0 923 275 A3 | 6/1999 |
| EP | 0 923 275 B1 | 6/1999 |
| JP | 11-235332 | 8/1999 |
| JP | 2005-65940 | 3/2005 |
| JP | 2009-66288 A | 4/2009 |
| JP | 2014-113475 | 6/2014 |

OTHER PUBLICATIONS

Office Action dated Feb. 12, 2019 in the corresponding Japanese Patent Application No. 2015-119678.

* cited by examiner

*Primary Examiner* — Don K Wong
(74) *Attorney, Agent, or Firm* — Oblon, McClelland, Maier & Neustadt, L.L.P.

(57) ABSTRACT

An X-ray apparatus includes a light emitting unit, input interface circuitry, and processing circuitry. The light emitting unit includes a light source. The input interface circuitry inputs an X-ray condition. The processing circuitry controls an emission state of the light emitting unit to change to one of at least three states based on the X-ray condition.

4 Claims, 6 Drawing Sheets

【FIG. 1】
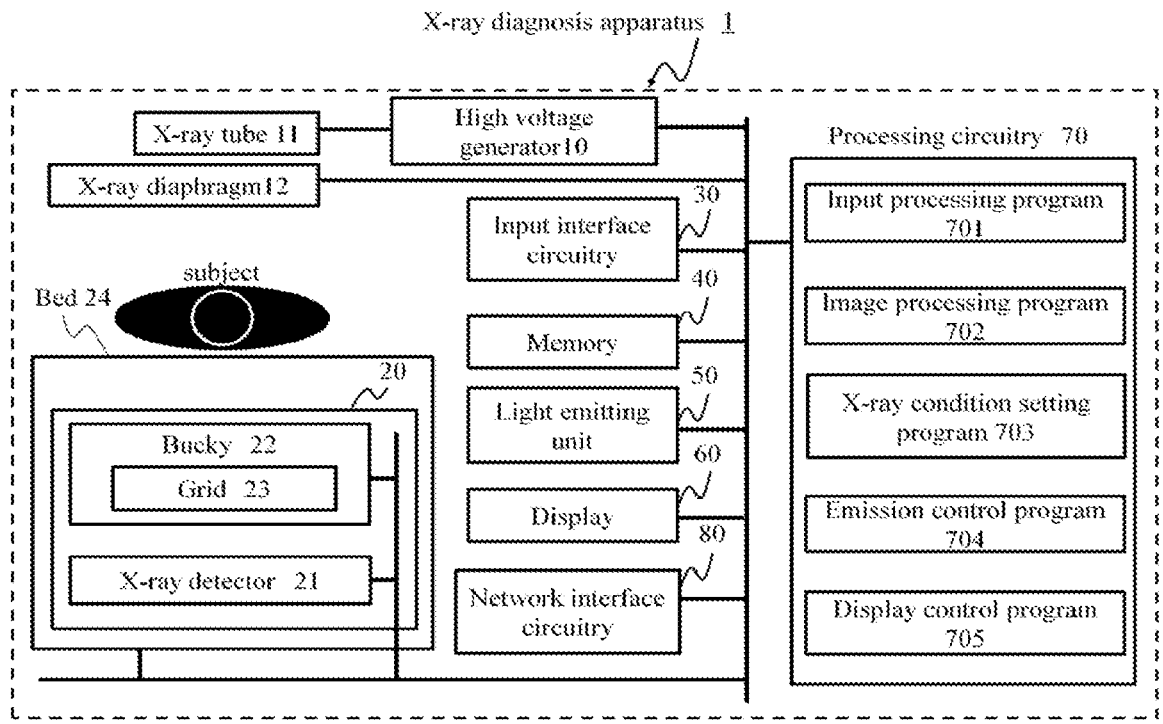
【FIG. 2】
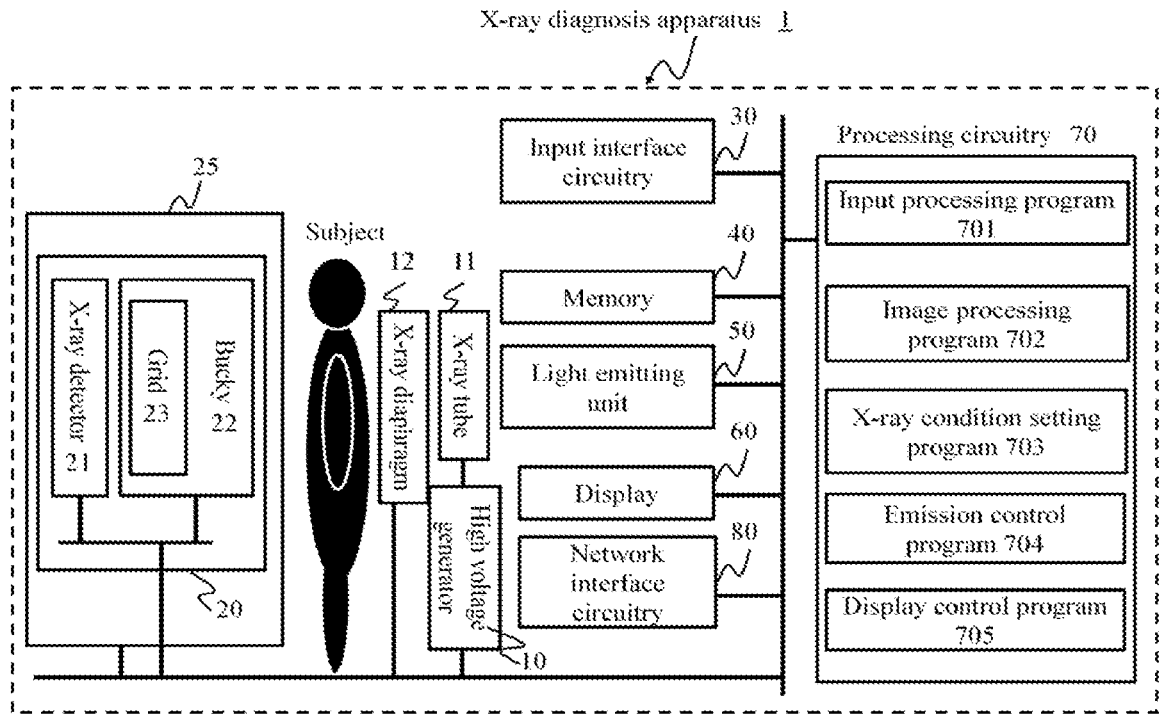

【FIG. 3】
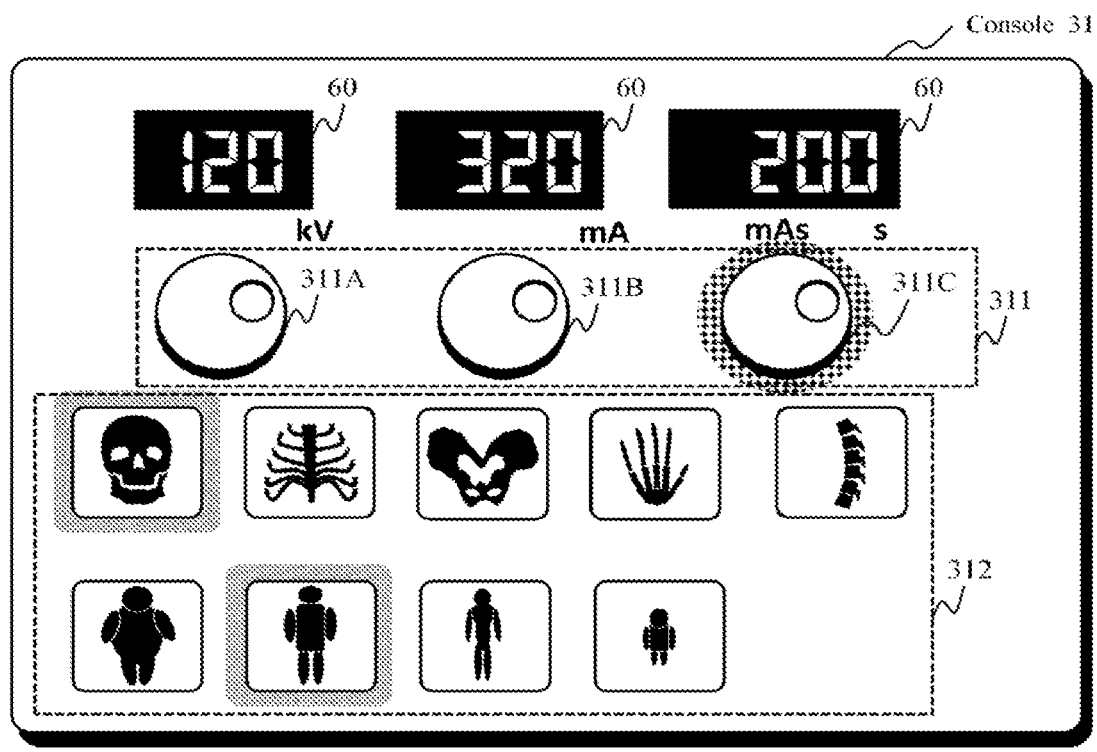
【FIG. 4】
| mAs value | ~5 | 6~10 | 11~15 | 16~ |
|---|---|---|---|---|
| Emission color | Blue | Green | Yellow | Orange |

【FIG. 5】
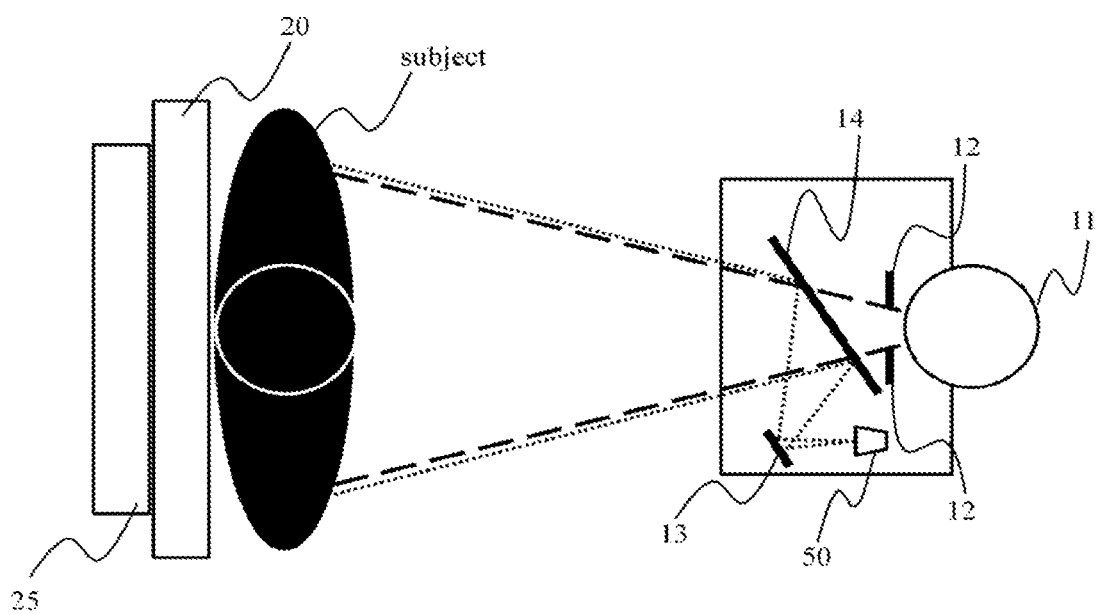
【FIG. 6】
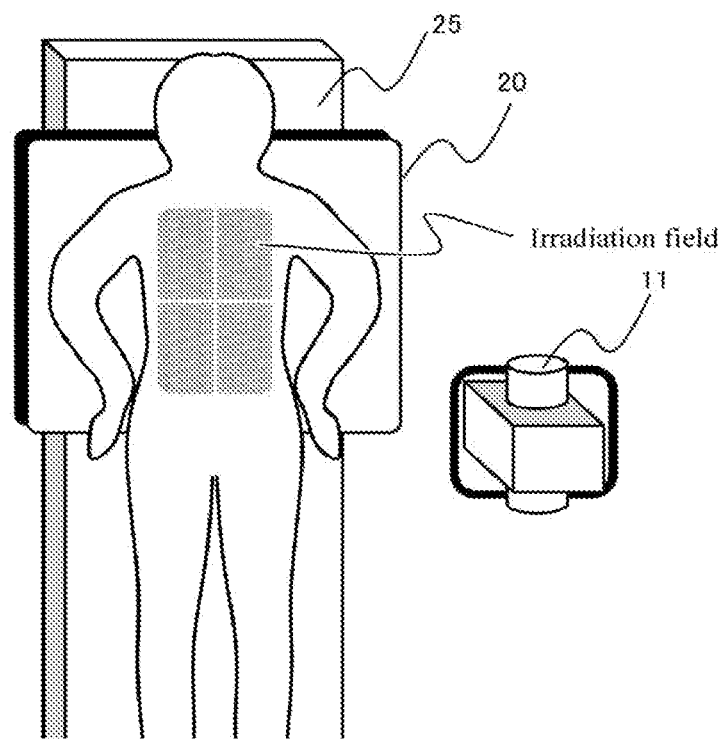

【FIG. 7】
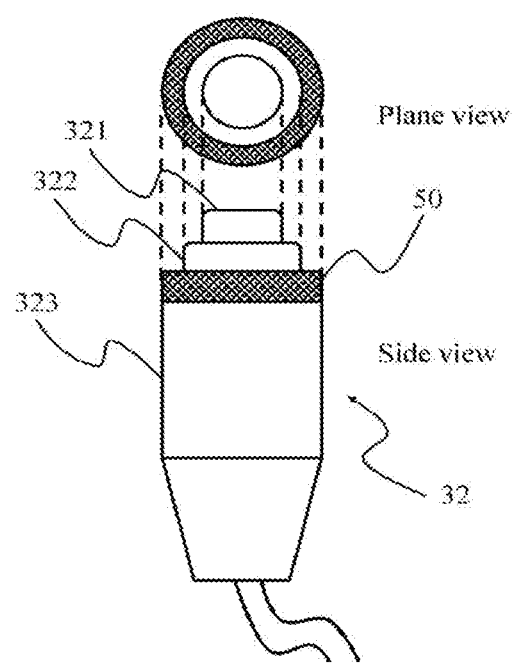

[FIG. 8]
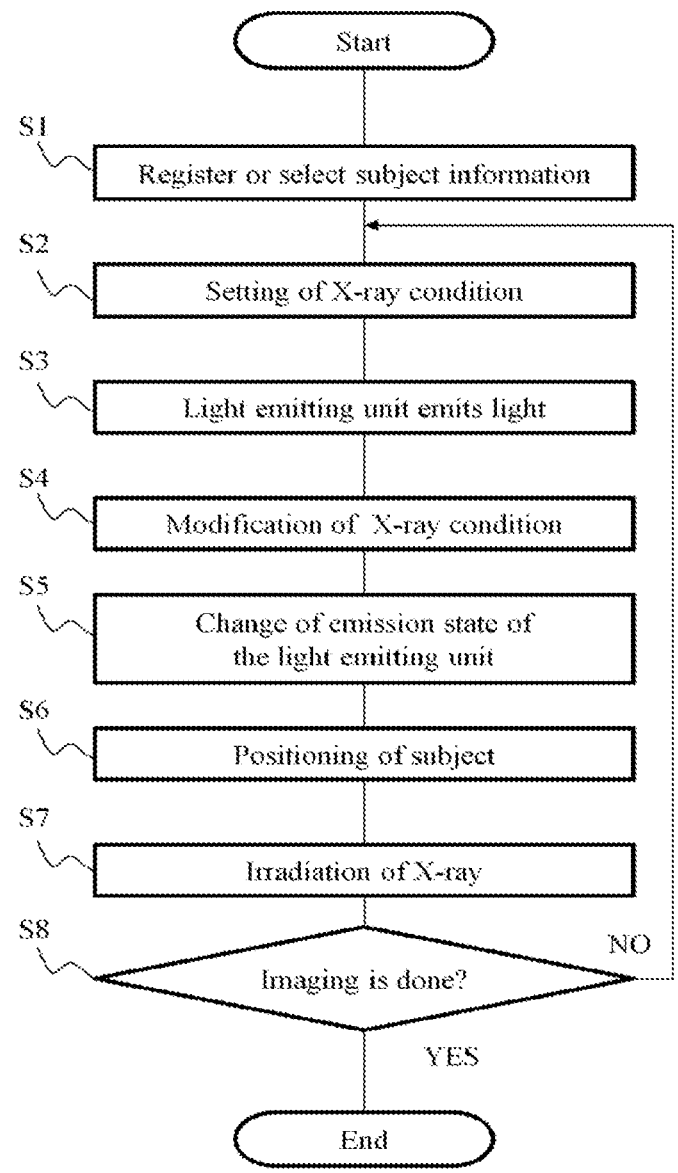

【FIG. 9】

| mAs<br>Body shape | ~2 | 3~5 | 6~10 | 11~15 | 16~20 | 21~ | Excess upper limit |
|---|---|---|---|---|---|---|---|
| Child | Blue | Green | Yellow | Orange | Orange | Orange | Red |
| Thin | Blue | Green | Green | Yellow | Orange | Orange | Red |
| Standard | Blue | Blue | Green | Yellow | Orange | Orange | Red |
| Fat | Blue | Blue | Green | Green | Yellow | Orange | Red | ns
X-RAY DIAGNOSIS APPARATUS

CROSS-REFERENCE TO RELATED APPLICATION

This application is based upon and claims the benefit of priority from Japanese Patent Application No. 2015-119678, filed Jun. 12, 2015, the entire contents of which are incorporated herein by reference.

FIELD

Exemplary embodiments described herein relate generally to an X-ray diagnosis apparatus.

BACKGROUND

An X-ray diagnosis apparatus irradiates a subject with X-rays and detects an intensity of the X-rays that have penetrated the subject to generate and display an image of the subject.

An operator, such as a doctor or a technician, prepares to image the subject based on a body shape and an imaging region of the subject. The preparation includes, for example, setting of the X-ray condition and positioning of an X-ray detector. An erroneous setting of the X-ray condition causes failure of imaging. Moreover, there is a risk that an exposure dose received by the subject increases when it is required to redo the imaging.

For example, a conventional X-ray diagnosis apparatus displays a value of the X-ray condition. In this case, the operator needs to check that the value of the X-ray condition displayed on the display is appropriate for the imaging. When the operator fails to check the value of the X-ray condition, an erroneous value can be used to irradiate the subject with the X-rays.

It is difficult, with the conventional X-ray diagnosis apparatus, to visually check the value of the X-ray condition to be appropriate before imaging.

BRIEF DESCRIPTION OF THE DRAWINGS

FIG. 1 is a block diagram illustrating a configuration of an X-ray diagnosis apparatus with a bed according to a first exemplary embodiment.

FIG. 2 is a block diagram illustrating a configuration of an X-ray diagnosis apparatus with a stand according to the first exemplary embodiment.

FIG. 3 is a drawing for explaining a structure of a console with a light emitting unit according to the first exemplary embodiment.

FIG. 4 is a table that a value of mAs is mapped to emission color of a light emitting unit according to the first exemplary embodiment.

FIG. 5 is a drawing seen from above for explaining a positional relationship between an X-ray tube and a light emitting unit according to the first exemplary embodiment.

FIG. 6 is a drawing for explaining light emission of the light emitting unit toward a standing subject according to the first exemplary embodiment.

FIG. 7 is a plane view and a side view of a hand switch according to the first exemplary embodiment.

FIG. 8 is a flow chart illustrating a flow of imaging the subject according to the first exemplary embodiment.

FIG. 9 is a table in which a combination between body shape information and the values of mAs is mapped to emission color of the light emitting unit according to a second exemplary embodiment.

DETAILED DESCRIPTION

An X-ray diagnosis apparatus 1 according to an exemplary embodiment comprises a light emitting unit 50, an input interface circuitry 30, and processing circuitry 70. The light emitting unit 50 includes a light source. The input interface circuitry 30 is configured to input an X-ray condition. The processing circuitry is configured to control an emission state of the light emitting unit 50 to change to one of at least three states, based on the X-ray condition.

Various exemplary embodiments will be described hereinafter with reference to the accompanying drawings.

First Exemplary Embodiment

An X-ray diagnosis apparatus 1 according to a first exemplary embodiment controls a light emission state of a light emitting unit 50. A light emission control program 704 of the processing circuitry 70 controls an emission state of the light emitting unit 50 based on changes of an X-ray condition.

Described below are a structure of the X-ray diagnosis apparatus 1 according to the first exemplary embodiment and a method of imaging the subject.

FIG. 1 is a block diagram illustrating a configuration of the X-ray diagnosis apparatus 1 with a bed 24. The X-ray diagnosis apparatus 1 includes a high voltage generator 10, an X-ray tube 11, an X-ray diaphragm 12, an X-ray detection unit 20, an input interface circuitry 30, a memory 40, a light emitting unit 50, a display 60, and processing circuitry 70. The processing circuitry 70 is configured to execute an input processing program 701, an imaging processing program 702, an X-ray condition setting program 703, a light emission control program 704, and a display control program 705. These programs are stored in a memory of the processing circuitry or the memory 40. The stored programs are developed and executed in the processing circuitry.

The processing circuitry can include, but is not limited to a CPU (Central Processing Unit), a GPU (Graphics Processing Unit), an ASIC (Application Specific Integrated Circuit), an SPLD (Simple Programmable Logic Device), a CPLD (Complex Programmable Logic Device), and a FPGA (Field Programmable Gate Array). The processing circuitry may include, but is not limited to simple circuitry or complex circuitry comprising a plurality of independent circuits.

An X-ray tube 11 generates X-rays by using a high voltage supplied by a high voltage generator 10. An X-ray diaphragm 12 is positioned near an irradiation opening of the X-ray tube 11. The X-ray diaphragm 12 adjusts an irradiation field of X-rays by shielding a part of the X-rays generated by the X-ray tube 11. A ratio at which X-rays penetrate the subject is adjusted by a voltage supplied to the X-ray tube 11. The X-ray exposure of output X-rays generated by the X-ray tube 11 is generally represented by a product of a tube current of the X-ray tube 11 and an imaging time, which is the time the X-ray tube 11 generates X-rays. Units for the tube current and the imaging time are "mA" and "s," therefore a value of the X-ray exposure is called "mAs."

The X-ray condition of the X-ray tube 11 is set by the X-ray condition setting program 703 of the processing circuitry 70. The X-ray condition setting program 703 reads out the X-ray condition, for example, from the memory 40 and/or from an external database system. The X-ray condition setting program 703 controls the high voltage generator 10 based on the X-ray condition. The X-ray condition includes, but is not limited to, a value of the current supplied to the X-ray tube 11, the value of mAs, and the imaging time.

A X-ray detection unit 20 includes an X-ray detector 21, a grid 23 to avoid deterioration of contrast of an X-ray image caused by scattered X-rays, and a bucky 22 to which the grid 23 inserts.

The X-ray detector 21 is, for example, an imaging plate or a FPD (Flat Panel Detector). The imaging plate is housed in a metal housing called a cassette. The imaging plate absorbs X-rays by a fluorescent material coated on it. A scanner generates an X-ray image by scanning the imaging plate. The FPD outputs digital data using the detected X-rays. For example, a direct conversion or an indirect conversion can be exploited to output the digital data. In the direct conversion, the FPD converts the X-rays directly to an electrical signal. In the indirect conversion, the FPD converts the X-rays to light by using a fluorescent material, then a photo-diode converts the light to an electrical signal. Digital data generated by the X-ray detector 21 is transmitted to an external server or the memory 40 and stored therein via a wired and/or wireless network by using the network interface circuitry 80. The digital data, in another example, can be directly transmitted to the memory 40 without using the network interface circuitry 80.

The grid 23 includes plates coated by a material, such as lead, which absorbs X-rays. The grid 23 is composed by the plates arranged in a lattice pattern, which prevents the X-ray detector 21 from receiving scattered X-rays. The grid 23 is inserted to the bucky 22 and configured to be able to adjust a position hereof. The bucky 22 may be configured to be able to swing.

The X-ray detection unit 20 mentioned above is installed inside or on a lower side of the bed 24. The X-ray detector 21 can be positioned on an upper side of the bed 24. When taking the X-ray image of a standing subject, the X-ray diagnosis apparatus 1 includes a stand 25 instead of the bed 24, as illustrated in FIG. 2. The stand 25 is capable of adjusting a position of the X-ray detection unit 20. For example, the stand 25 adjusts the vertical position of the X-ray detection unit 20.

The input interface circuitry 30 receives an input from the operator and generates an input signal according to the received input. The input interface circuitry 30 is, for example, a mouse, a trackball, a joystick, a push button, a dial, a touch panel, a touchpad, a keyboard, a hand switch, or a foot switch. The input signal is sent to an input processing program 701 of the processing circuitry 70. When the input interface circuitry 30 is the touch panel, the input interface circuitry 30 is also used for a display 60.

The input processing program 701 executed in the processing circuitry 70 receives the input signal generated by the input interface circuitry 30, and converts the input signal to input data that can be processed by memory 40 or each program executed in the processing circuitry 70.

The image processing program 702 executed in the processing circuitry 70, for example, eliminates noise of an X-ray image or adjusts a contrast of an X-ray image. The X-ray image is acquired by the X-ray detector 21 such as an FPD or by network interface circuitry 80.

A display control program 705 executed in the processing circuitry 70 controls contents of a display 60. The contents displayed by the display 60 are, for example, the input data generated by the input processing program 701, or input data stored in the memory 40.

The memory 40 is, for example, a magnetic disk, such as a hard disk, or a flash memory, such as a solid state drive, a USB memory, and a memory card, etc. In another example, the memory 40 is configured to be able to read and/or write data to/from an optical disk such as CD or DVD. The memory 40 can be connected to each unit of the X-ray diagnosis apparatus 1 by using internal circuitry and/or external circuitry.

A light emitting unit 50 includes a light source. The light source may include, but is not limited to, a halogen lamp, a light emitting diode (LED), and an incandescent bulb. The emission state of the light emitting unit 50 is controlled by the emission control program 704 of the processing circuitry 70. The emission control program 704 controls the emission state of the light emitting unit 50, such as emission color, brightness, or lighting state (blinking, continuous lighting, etc.). The light emitting unit 50 is included in, for example, (1) a console 31, (2) an irradiation field lamp, and (3) a hand switch 32. Detailed examples of the light emitting unit 50 are described below.

(1) A Light Emitting Unit 50 Included in a Console 31

FIG. 3 illustrates dial 311, push button area 312, and display 60, which are included in a console 31. The dial 311 comprises a plurality of dials and is configured to be able to change a value of the X-ray condition. The push button area 312 comprises a plurality of push buttons, and is configured to be able to set an imaging region and/or body shape information. The display 60 displays the value of the X-ray condition. The light source illuminates dial 311, push buttons 312, and/or display 60 according to changes of the values of the X-ray condition.

(1-a) The Light Emitting Unit 50 Illuminating the Dial 311

The dial 311 is configured to be able to change the values of the X-ray condition according to rotation of the dial 311. For example, the left-most dial 311A illustrated in FIG. 3 is configured to be able to change a tube voltage. When the dial 311A turns right, the tube voltage increases. When the dial 311A turns left, the tube voltage decreases. A middle dial 311B illustrated in FIG. 3 corresponds to a tube current. A right most dial 311C illustrated in FIG. 3 corresponds to values of mAs. The values corresponding to dial 311B and 311C change as well as the values corresponding to the dial 311A.

For example, the light source that illuminates the dial 311 is installed under the dial 311, being provided in the console 31. When the light source is configured to illuminate an edge of dial 311, the edge of dial 311 is, for example, formed by a light-transmitting material. A light emitted by the light source leaks out from the edge of the dial 311 toward the outside of the console 31. When the light source is configured to illuminate the dial 311 itself, the dial 311 is formed by a light-transmitting material. Then, the light emitted by the light source, which comes from under the dial 311, illuminates the dial 311. When each of dials 311A, 311B, and 311C illustrated in FIG. 3 is illuminated independently by a light source, the light sources are configured not to interfere with each other. For example, a light-shielding material is provided between the light sources.

An emission state of the light emission unit 50 can be changed to have a plurality of distinct values or states. The emission state of the light emitting unit 50 is, for example, controlled by the emission control program 704 by referring to a table in which the X-ray condition is mapped to the emission state. FIG. 4 illustrates an example of the table that takes values of mAs as the X-ray condition and maps them to emission colors as the emission state. According to FIG.

4, the emission control program 704 controls the light emitting unit 50 to emit yellow light when the value of mAs is 13 mAs. Preferably, the emission control program 704 controls the light emitting unit 50 to emit cool color light when the value of mAs is low. On the other hand, the emission control program 704 controls the light emitting unit 50 to emit warm color light when the value of mAs is high. The higher the value of the mAs becomes, the warmer the emission color becomes in a plurality of increments. The light emitting unit 50, for example, includes a multicolor LED, which can change the emission color. In another example, the light emitting unit 50 includes a white LED and color films. The emission color can be changed by using a plurality of color films, so that the light of the white LED transmitting through the color film is colored.

The emission control program 704 can be configured to control, in other examples, the brightness of the light emitting unit 50 or the lighting state of the light emitting unit 50. When the emission control program 704 controls the brightness, the emission control program 704 exploits a table similar to the table illustrated in FIG. 4. The table for controlling brightness can be provided by replacing the emission color with brightness in FIG. 4. For example, the emission control program 704 controls the light emitting unit 50 to become brighter with increasing values of mAs. When the emission control program 704 controls the lighting state, the emission control program 704 exploits a table similar to the table illustrated in FIG. 4. The table for controlling the lighting state can be provided by replacing the emission color with the lighting state in FIG. 4. For example, the emission control program 704 controls the light emitting unit 50 to blink more frequently with increasing values of mAs. In another example, the emission control program 704 controls the light emitting unit 50 to emit light continuously when the value of mAs is under a predetermined value, and to blink when the value of mAs is over the predetermined value.

The emission state can be provided by a combination of the emission color, the brightness, and the lighting state. For example, the light emitting unit 50 can emit blue light with low brightness when the value of the X-ray condition is low. On the other hand, the light emitting unit 50 can emit red light with high brightness when the value of the X-ray condition is high.

(1-b) The Light Emitting Unit 50 Illuminating Push Button 312

The push button area 312 is associated with the data such as an imaging region of the subject, body shape information, etc. When the operator pushes a push button in push button area 312, the associated data is sent to the input processing program 701. For example, the data, representing that the imaging region is the head is sent to the input processing program 701 when the push button having an illustration of a skull is pushed. The imaging region may include, but is not limited to, head, chest, leg, hand, spine, and stomach. In another example, the data representing the body shape of the subject is sent to the input processing program 701 when a push button is pushed. The light emitting unit 50 illuminating the push button area 312 is arranged as well as the dial 311 described in (1-a).

The emission state of the light emitting unit 50 illuminating the push button area 312 has at least three states according to the X-ray condition associated to the push button 312. For example, suppose that a push button having an illustration of a rib, representing that the imaging region is chest, is associated with the X-ray condition that a tube current and an imaging time are 200 mA and 0.02 seconds, respectively. The value of mAs is 4 mAs according to a product of the tube current and the imaging time. When the push button is pushed, the emission control program 704 controls the light emitting unit 50 to emit blue light based on the table illustrated in FIG. 4 in which the values of mAs are mapped to the emission colors.

The emission control program 704 controls the emission state (emission color, brightness, and lighting state, etc.) of the light emitting unit 50 illuminating the push buttons as well as the dial 311.

(1-c) The Light Emitting Unit 50 Illuminating Display 60

The display 50 displays the value of the X-ray condition associated with the push button area 312 or that adjusted by the dial 311. The display 60 is a seven-segment display. The seven-segment display displays a number represented by four vertical bars and three horizontal bars.

One example of the light emitting unit 50 illuminating display 60 is a backlight. A surface of the seven-segment display is formed by a light-transmitting material. An LED as the backlight is placed under the surface of the seven-segment display. Another example of the light emitting unit 50 is arrayed along the seven segments. The arrayed light emitting unit 50 directly represents a number.

The emission state of the light emitting unit 50 illuminating display 60 is controlled to have one of at least three states by the emission control program 704. The emission control program 704 controls the light emitting unit 50 similarly to the case of the dial 311. The emission state includes, but is not limited to, emission color, brightness, and lighting state of the light emitting unit 50.

The aforementioned display 60 is not limited to a seven-segment display. The display 60 can be a liquid crystal display that displays values such as the X-ray condition.

(2) A Light Emitting Unit 50 Included in an Irradiation Field Lamp

FIG. 5 illustrates a standing subject, an X-ray tube, and the light emitting unit 50 from above. The X-ray tube 11 irradiates the subject standing in front of the X-ray detection unit 20, which is supported by the stand 25. An irradiation field, which is a field where the subject receives X-rays, is adjusted by the X-ray diaphragm 12. The X-ray diaphragm adjusts the irradiation field, blocking a part of the X-rays generated by the X-ray tube 11.

The irradiation field is configured to be easy to visually understand by the operator, illuminating the subject by an irradiation field lamp. A detailed example of the irradiation field lamp is described below.

The light emitting unit 50, for example, emits light toward a reflector 13 illustrated in FIG. 5. The light is visible light in this example. The light reflected by the reflector 13 is reflected again by a half mirror 14 that is placed at a side at which the X-ray tube 11 irradiates the subject. The light reflected by the half mirror 14 arrives at the subject. The half mirror 14 is formed by a material that reflects visible light, but that X-rays penetrate. A region illuminated by the light emitting unit 50 is almost the same as the irradiation field of the X-rays.

FIG. 6 illustrates the subject illuminated by the light emitting unit 50 from the back. FIG. 6 is one example of imaging a chest of the subject by irradiating the subject from the back. The irradiation field, which is a chest region on the back of the subject, is illuminated by the light emitting unit 50. Cross lines on the illuminated region represent a center of the irradiation field. The cross lines are optional in this exemplary embodiment.

The emission state of the light emitting unit 50 is, for example, decided by the emission control program 704 referring to the table illustrated in FIG. 4. The emission state is decided from at least three states. For example, when a value of mAs is 13 mAs, the emission control program 704 controls the light emitting unit 50 to emit yellow light. The subject is illuminated by the yellow light. Preferably, the emission control program 704 controls the light emitting unit 50 to emit light that is close to red when the value of mAs increases. The color close to red represents a warning to the operator. The light emitting unit 50, for example, comprises a multicolor LED so that the color can be variable. For another example, the light emitting unit 50 comprises a white LED and a plurality of films. Each of the films has different color and is placed at a side at which the X-ray tube 11 irradiates the subject. The film can be switched according to the emission state.

The emission control program 704 controls an emission color of the light emitting unit 50. However, the emission state is not limited to the emission color, but also includes brightness and a lighting state. When the emission control program 704 controls the brightness, the emission control program 704 refers to a table similar to that illustrated in FIG. 4. In this case, the table represents a relationship between the values of the X-ray conditions and values of brightness, instead of the emission color. For example, the emission control program 704 controls the light emitting unit 50 to emit light brighter when the value of mAs increases. When the emission control program 704 controls the lighting state, the emission control program 704 refers to a table similar to that illustrated in FIG. 4. In this case, the table represents a relationship between X-ray conditions and values of a lighting state instead of the emission color. For example, the emission control program 704 controls the light emitting unit 50 to blink more frequently when the value of mAs increases. For another example, the emission control program 704 controls the light emitting unit 50 to emit light continuously when the value of mAs is under a predetermined value, and to blink when the value of mAs is over the predetermined value.

(3) A Light Emitting Unit 50 Included in a Hand Switch 32

A hand switch 32 to operate irradiation of X-rays based on the X-ray condition is illustrated in FIG. 7. The hand switch 32 is illustrated from a plan view and a side view. The hand switch 32 includes a grip 323, a ready switch 321, and an irradiation switch 322. The ready switch 321 sets the X-ray tube 11 ready to generate X-rays. The irradiation switch 322 operates the irradiation of X-rays. The light emitting unit 50 is, for example, placed on top of the grip 323. Emitted light of the light emitting unit 50 is configured to be visible either from above or from the side. The light emitting unit 50 is, for example, provided in the hand switch 32. A part of the grip 323 that is near the irradiation switch 322 is formed by a light-transmitting material. The position of the light emitting unit 50 in not limited to being near the irradiation switch 322, but can also be on any part of the hand switch 32. Preferably, the light emitting unit 50 is positioned on a place that is not hidden by hands of the operator. The emission control program 704 controls the emission state of the light emitting unit 50 in a similar way to the irradiation field lamp as the light emitting unit 50.

A method of imaging a subject based on input and/or selection of subject information to image the subject is described as follows referring to the flowchart illustrated in FIG. 8. The console 31, the irradiation field lamp, and the hand switch 32 each include the light emitting unit 50.

In Step S1, subject information is registered or selected by the operator. The subject information includes, but is not limited to, a subject ID, name, height, weight, gender, birth day, and age. The subject information is, for example, selected from a database system connected via network interface circuitry 80. The network system is, for example, a Hospital Information System (HIS) or a Radiology Information System (RIS). In another example, the subject information can be selected from the memory 40. In another example, the subject information can be registered based on the input information inputted by the operator.

In Step S2, an X-ray condition is set by the operator. For example, the X-ray condition is acquired from the HIS or the RIS via the network interface circuitry 80. In another example, the X-ray condition is selected from the data stored in the memory 40.

In Step S3, the light emitting unit 50 emits light under control of the emission control program 704. The operator stands or sits in front of the console 313 and sets the X-ray condition so that the operator can visually check the emission state of the light emitting unit 50.

In Step S4, the input interface circuitry 40 accepts modification of the X-ray condition. The operator modifies the X-ray condition set in Step S2 as needed based on body shape information. For example, the console 31 as the input interface circuitry 30 accepts increasing or decreasing of a tube current and/or a tube voltage according to the rotating dial 311.

In Step S5, the emission state of the light emitting unit 50 is changed under control of the emission control program 704. The emission control program 704 controls the light emitting unit 50 to change the emission state according to the X-ray condition after the change in Step S4 by using the input interface circuitry 30. Thus, the operator can visually check that the X-ray condition has changed by changing the emission state of the light emitting unit 50 that is housed in the console 31.

In Step S6, an imaging position of the subject is adjusted by the operator. For example, the operator adjusts an irradiation direction of the X-ray tube 11, a position of the X-ray detection unit 20 supported by the stand, and/or a posture of the subject. When the operator adjusts the imaging position, the operator can visually check the emission state of the light emitting unit 50 that is included in the irradiation field lamp by watching the light illuminated toward the subject.

In Step S7, the X-ray tube 11 generates X-rays according to the X-ray condition set in the steps described above. Irradiation of the X-rays is operated by the hand switch 32. First, when the ready switch 321 is pushed by the operator, the high voltage generator 10 supplies the X-ray tube 11 with the high voltage based on the X-ray condition. Next, when the irradiation switch 322 is pushed, the X-ray tube 11 generates X-rays and imaging is carried out. The operator can check the emission state of the light emitting unit 50 housed in the hand switch 32 when the operator holds the hand switch 32 and pushes the ready switch 321 and the irradiation switch 322.

In Step S8, the X-ray diagnosis apparatus 1 determines whether the imaging is to be continued. When the imaging is continued, the X-ray diagnosis apparatus 1 acquires the X-ray condition of the next imaging procedure, returning to Step S2. When no more imaging is continued, the process ends.

In the aforementioned flowchart, the X-ray diagnosis apparatus 1 includes the light emitting unit 50 included in the console 31, the irradiation lamp, and the hand switch 32. However, so far as at least one light emitting unit 50 as mentioned above is included in the X-ray diagnosis apparatus 1, the operator can visually check that the value of the X-ray condition is appropriate. When a plurality of the light emitting units 50 are included in the X-ray diagnosis apparatus 1, the opportunity for the operator to visually check the value of the X-ray condition is appropriate, so that the risks of irradiation of the X-rays caused by the inappropriate value are decreased.

The X-ray diagnosis apparatus 1 described above includes an X-ray detection unit 20, a bed 24, and a stand 25. However, an X-ray diagnosis apparatus that does not include these units also provides an X-ray diagnosis apparatus in which it is easy to visually check the X-ray condition for the operator according to this exemplary embodiment. Further, the X-ray diagnosis apparatus is configured to be mobile, such as a mobile X-ray device.

In the first exemplary embodiment mentioned above, the emission control program 704 executed in the processing circuitry 70 controls the light emitting unit 50 to change the emission state based on the changes of the values of the X-ray condition. Thus, the operator can visually check that the value of the X-ray condition is appropriate. Moreover, the X-ray diagnosis apparatus 1 can prevent the operator from executing the X-ray irradiation based on an inappropriate value of the X-ray condition. The light emitting unit 50 is positioned so as to be easily seen, so that the operator does not fail to check the emission state of the light emitting unit 50.

The X-ray diagnosis apparatus 1 makes it easy to visually check the value of the X-ray condition to prevent the subject from being imaging by the wrong amount of X-rays. Thus, the X-ray diagnosis apparatus 1 prevents the subject from an excessive exposure dose caused by having to reperform the imaging.

Second Exemplary Embodiment

The X-ray diagnosis apparatus 1 in the second exemplary embodiment controls the emission state of the light emitting unit 50 based on a combination of the subject information and the X-ray condition. The contents overlapping with the first exemplary embodiment are omitted in the second exemplary embodiment. In regard to the reference signs in the figures, the same reference signs as in the first exemplary embodiment are used.

In this exemplary embodiment, for example, the emission control program 704 decides the emission color of the light emitting unit 50 based on a combination of the value of mAs and the body shape information of the subject. The emission control program 704 controls the emission color of the light emitting unit 50 referring to the table shown in FIG. 9. In FIG. 9, the table maps combinations of the body shape information of the subject and the value of mAs to an emission color of the light emitting unit 50.

The table shown in FIG. 9 is a table in which the body shape information of the subject is added to the table shown in FIG. 4. The table is used to decide the emission state of the light emitting unit 50. The body shape information is one of the reference values to check that the X-ray condition is appropriate. Generally, when the body shape of the subject is large and thick, the contrast of the X-ray image becomes insufficient. A default value of an X-ray exposure that is the standard value is insufficient in such a case, so that the tube voltage should be set to a higher value than the standard value. On the other hand, when the body shape is small and thin, such as for a child, the X-ray image becomes contrast excessive. The default value of the X-ray exposure is too high, so that the tube voltage should be set to a lower value than the standard value.

In the following, the step in which the emission control program 704 controls the light emitting unit 50 is explained. The flow from registration/selection of the subject information to X-ray irradiation is almost the same as in the first exemplary embodiment, except for the step described below.

In Step S2, for example, the push button 312 corresponding to the body shape "Child" and the push button 312 corresponding to imaging region "Chest" are pushed. When each push button 312 is pushed, the X-ray condition setting program 703 reads data of the X-ray condition from the memory 40 or an external database system such as HIS or RIS via network interface circuitry 80. For example, the imaging of a child's chest using the X-ray condition that the tube current is 200 mA and the imaging time is 0.025 second. The value of mAs is 5 mAs, which is a product of the tube current and the imaging time. Then the emission control program 704 controls the light emitting unit 50 to emit green light, by referring to the table shown in FIG. 9.

The emission control program 704 controls the light emitting unit 50 to emit a different color based on the subject's body shape information, even when the same value of mAs is set because the maximum permissive dose is different depending on the body shape. For example, when the value of mAs is in the range from 11 to 15, the light emitting unit 50 emits orange light when the body shape is "Child," emits yellow light when the body shape is "Thin" or "Standard," and emits green light when the body shape is "Fat," by referring to the table in FIG. 9.

The emission control program 704 can be configured to control not only the emission color, but also the brightness or the lighting state of the light emitting unit 50. When the emission control program 704 controls the brightness, the emission control program 704 uses a table similar to the table illustrated in FIG. 9. The table for controlling brightness can be provided by replacing the emission color with brightness in FIG. 9. When the emission control program 704 controls the lighting state, the table for controlling the lighting state is provided by replacing the emission color in the table in FIG. 9 to the lighting state. For example, the emission control program 704 controls the light emitting unit 50 to blink more frequently with increasing values of mAs. The table illustrated in FIG. 9 can be created for each imaging region and X-ray condition. Thus, the emission control program 704 can control the emission state of the light emitting unit 50 in accordance with the maximum permissive dose, which is different depending on each imaging region.

When an upper limit of the X-ray condition is set for each body shape information, the light emitting unit 50, for example, emits red light when the X-ray condition exceeds the upper limit. Preferably, a color not used in the range of permissive exposure dose is used when the X-ray condition exceeds the upper limit for the purpose of preventing the subject from being exposed to excessive X-rays. For example, in the range of the permissive values of mAs, the light emitting unit 50 emits light whose color is between blue and orange, and the light emitting unit 50 emits red light when the value of mAs exceeds the upper limit. The method to alert that the X-ray condition exceeds the upper limit is not limited to emitting specific light, but also to blinking only when an excessive X-ray condition exits.

In the above description, the emission color of the light emitting unit 50 is controlled according to a combination of the subject information and the value of mAs. However, the tube voltage, the tube current, or the imaging time can be also used to create the table that decides the emission color. Moreover, the combination of these elements can be mapped to the emission color. The table to map the the body shape information to the emission color of the light emitting unit 50 can be created depending on the model of the X-ray detector 21. In this case, the emission control program 704 reads out identification information from the X-ray detector, and acquires the table corresponding to the model from the database, such as the memory 40 and/or the external database. Then, the emission control program 704 decides the emission state of the light emitting unit 50 by referring to the table.

In the second exemplary embodiment mentioned above, the emission control program 704 controls the emission state of the light emitting unit 50 or the display 60 based on a combination of the body shape information of the subject and the X-ray condition. Thus, the X-ray diagnosis apparatus 1 makes it easy for the operator to visually check that the X-ray condition is appropriate in consideration of the body shape information.

Third Exemplary Embodiment

The X-ray diagnosis apparatus 1 in the third exemplary embodiment controls the emission state of the light emitting unit 50 based on the ready state of the X-ray detection unit 20. The contents overlapping with the first and second exemplary embodiment are omitted in the third exemplary embodiment. In regard to the reference signs in the figures, the same reference signs as the first and second exemplary embodiment are used.

The emission control program 704 detects the ready state of the X-ray detection unit 20, which is described below, and controls the emission state of the light emitting unit 50.

(1) Connection State of X-ray Detector 21

The emission control program 704 controls the emission state of the light emitting unit 50 based on the connection between the X-ray detector 21 and other units of the X-ray diagnosis apparatus 1. The connection status is, for example, the state that the X-ray detector 21 is inserted to a predetermined position of the X-ray detection unit 20. In another example, the connection state is the state that the X-ray detector 21 is correctly communicating with other units of the X-ray diagnosis apparatus 1 or the database system, such as HIS or RIS, via the network interface circuitry 80. When the X-ray detector 21 is connected to some units of the X-ray diagnosis apparatus 1 with a cable, the connection is confirmed by circuitry. The emission control program 704 reads out the identification information from the X-ray detector 21, and judges that the correct X-ray detector 21 is connected with the X-ray detection unit 20.

(2) Position of X-ray Detector 21

The emission control program 704 judges that the X-ray detector 21 is positioned to be able to receive the X-rays generated by the X-ray tube 11. For example, when the X-ray diagnosis apparatus 1 includes the bed 24 and the stand 25, there are two positions for the X-ray detector 21 to be positioned. The X-ray detector 21 needs to be positioned at the position used for imaging, where the subject is placed. When the subject is placed on the bed 24, the X-ray detector 21 should be positioned at the X-ray detection unit 20 provided in the bed 24. For example, when the X-ray detector 21 is positioned at the X-ray detection unit 20 provided in the stand 25, although the X-ray tube 11 is to generate X-rays toward the bed 24, the emission control program 704 judges that the position of the X-ray detector 21 is incorrect.

In the above description, the emission control program 704 detects an error when the X-ray detector 21 is not positioned at a place to be able to receive the X-rays generated by the X-ray tube 11. In another example, when the X-ray detector 21 is mounted on the top of the bed 24, the emission control program 704 detects an error when another X-ray detector 21 is inserted inside of the bed 24. If the X-ray tube 11 generates X-rays to the mounted X-ray detector 21 while another X-ray detector 21 already imaged is inserted inside of the bed 24, the image of the X-ray detector 21 already imaged receives X-rays again. That is, the emission control program 704 prevents the X-ray detector 21 already imaged from being irradiated again.

(3) Insert Status of Grid 23 Installed in Bucky 22

The emission control program 704 judges that the grid 23 is correctly inserted to the bucky 22. Whether the grid 23 is correctly inserted in the predetermined position is judged by a push type switch or an infrared sensor, for example.

The X-ray diagnosis apparatus 1 detects at least one ready state from (1) to (3), and then the emission control program 704 controls the emission state of the light emitting unit 50. In case of combining the state from (1) to (3) described in this exemplary embodiment and the first or second exemplary embodiment, the emission control program 704 refers to the table so that the combination between the X-ray condition and the ready state of the X-ray detection unit 20 is mapped to the emission state. For example, when the X-ray condition is mapped with a blue color, the light emitting unit 50 blinks with blue light when the ready state of the X-ray detection unit 20 is incorrect, and emits blue light continuously when the ready state of the X-ray detection unit 20 is correct. Thus, the operator can visually understand what causes the changes of the emission state of the light emitting unit 50.

For example, the light emitting unit 50 is included in the console 31, the irradiation field lamp, or the hand switch 32 as described in the first exemplary embodiment. For example, the emission color or the lighting state of the light emitting unit 50 represents whether the ready state of the X-ray detection unit 20 is correct. When the emission color represents the ready state of the X-ray detection unit 20, for example, the light emitting unit 50 emits white light when the ready state is correct, and emits red light when the ready state is incorrect. In another example, when the lighting state represents the ready state, the light emitting unit 50 emits light continuously, and blinks when the ready state is incorrect.

In the third exemplary embodiment mentioned above, the emission control program 704 controls the emission state of the light emitting unit 50 based on the ready state of the X-ray detection unit 20. Thus, the operator can visually check the ready state of the X-ray detector 21 or the grid 23 when the operator prepares the imaging. Moreover, redoing imaging caused by a fault of the ready state of the X-ray detection unit 20 is prevented.

According to the X-ray diagnosis apparatus 1 of at least one of the exemplary embodiments described above, an operator can easily check that the value of the X-ray condition is appropriate before imaging.

While certain exemplary embodiments have been described, these exemplary embodiments have been presented by way of example only, and are not intended to limit the scope of the inventions. Indeed, the novel exemplary embodiments described herein may be embodied in a variety of other forms; furthermore, various omissions, substitutions and changes in the form of the exemplary embodiments described herein may be made without departing from the spirit of the inventions. The accompanying claims and their equivalents are intended to cover such forms or modifications as would fall within the scope and spirit of the inventions.

What is claimed is:

1. An X-ray diagnosis apparatus, comprising:
a light emitting unit including a light source, wherein the light emitting unit emits light to illuminate an irradiation field of an X-ray and is provided in a console configured to accept input by an operator;
input interface circuitry configured to receive input of an X-ray condition; and
processing circuitry configured to control an emission state of the light emitting unit to change to one of at least three states, based on the X-ray condition.

2. An X-ray diagnosis apparatus, comprising:
a light emitting unit including a light source, wherein the light emitting unit emits light to illuminate an irradiation field of an X-ray and is provided in a hand switch configured to at least one of set an X-ray tube ready to generate X-rays and operate irradiation of X-rays;
input interface circuitry configured to receive input of an X-ray condition; and
processing circuitry configured to control an emission state of the light emitting unit to change to one of at least three states, based on the X-ray condition.

3. The X-ray diagnosis apparatus according to claim 2, wherein the light emitting unit is provided in at least one of a ready switch and an irradiation switch.

4. An X-ray diagnosis apparatus, comprising:
a light emitting unit including a light source;
an X-ray detection unit housing an X-ray detector; and
processing circuitry configured to control an emission state of the light emitting unit to change to one at least three states, based on a ready state of the X-ray detection unit,
wherein the X-ray detection unit comprises a grid to avoid deterioration of a contrast of an X-ray image caused by scattered X-rays and a bucky into which the grid inserts, and the processing circuitry is further configured to judge the ready state based on whether the grid is correctly inserted into the bucky.

* * * * *